(12) United States Patent
Whitehurst et al.

(10) Patent No.: US 7,054,692 B1
(45) Date of Patent: May 30, 2006

(54) FIXATION DEVICE FOR IMPLANTABLE MICRODEVICES

(75) Inventors: Todd K Whitehurst, Frazier Park, CA (US); James P McGivern, Stevenson Ranch, CA (US)

(73) Assignee: Advanced Bionics Corporation, Valencia, CA (US)

( * ) Notice: Subject to any disclaimer, the term of this patent is extended or adjusted under 35 U.S.C. 154(b) by 477 days.

(21) Appl. No.: 10/146,332

(22) Filed: May 15, 2002

Related U.S. Application Data

(60) Provisional application No. 60/300,401, filed on Jun. 22, 2001.

(51) Int. Cl.
*A61N 1/05* (2006.01)

(52) U.S. Cl. .................. 607/149; 607/36; 607/118; 607/116; 607/2; 600/386

(58) Field of Classification Search .............. 607/1–3, 607/36, 46, 118, 120, 125, 126, 149, 116; 600/386; 128/898; 606/151, 152, 154; 224/200
See application file for complete search history.

(56) References Cited

U.S. PATENT DOCUMENTS

| | | | |
|---|---|---|---|
| 281,482 A * | 7/1883 | Freeman .................. | 383/6 |
| 3,654,933 A * | 4/1972 | Hagfors .................. | 607/118 |
| 3,683,933 A * | 8/1972 | Mansfield ................ | 607/36 |
| 3,943,936 A * | 3/1976 | Rasor et al. ............. | 607/35 |
| 4,258,724 A * | 3/1981 | Balat et al. ............. | 607/128 |
| 4,289,144 A * | 9/1981 | Gilman .................. | 607/123 |
| 4,301,815 A | 11/1981 | Doring | |
| 4,341,221 A * | 7/1982 | Testerman .............. | 600/377 |
| 4,402,329 A * | 9/1983 | Williams ................ | 607/123 |
| 4,430,999 A | 2/1984 | Brighton et al. | |
| 4,590,946 A | 5/1986 | Loeb | |
| 4,602,624 A | 7/1986 | Naples et al. | |
| 4,608,985 A | 9/1986 | Crish et al. | |
| 4,628,942 A | 12/1986 | Sweeney et al. | |
| 4,628,944 A | 12/1986 | MacGregor et al. | |
| 4,867,164 A | 9/1989 | Zabara | |
| 4,913,164 A | 4/1990 | Greene et al. | |
| 5,090,422 A | 2/1992 | Dahl et al. | |
| 5,092,332 A * | 3/1992 | Lee et al. ............... | 600/377 |
| 5,193,539 A | 3/1993 | Schulman et al. | |
| 5,193,540 A | 3/1993 | Schulman et al. | |
| 5,199,430 A | 4/1993 | Fang et al. | |
| 5,312,439 A | 5/1994 | Loeb | |

(Continued)

FOREIGN PATENT DOCUMENTS

WO WO-97/29802 A2 8/1997

(Continued)

*Primary Examiner*—Kennedy Schaetzle
(74) *Attorney, Agent, or Firm*—Kenneth L. Green; Peter K. Johnson; Bryant R. Gold

(57) ABSTRACT

A fixation device fixes the position of an implantable microminiature device residing proximally to a target site such as a nerve or a muscle. In one embodiment, the device comprises a sheath and a means for attaching the device to adjacent tissue. The means for attaching may be any one of several embodiments including one or more grasping members, a combination of grasping members and one or more helices, or an extension adapted to accept a suture. In another embodiment, the fixation device comprises an assembly residing in the implantation pathway, behind the stimulation device, thus preventing retreat of the stimulation device in the pathway. In a preferred use, the fixation device fixes the position of a microstimulator component of a Peripheral Nerve Stimulation (PNS) system.

22 Claims, 6 Drawing Sheets

U.S. PATENT DOCUMENTS

| | | | |
|---|---|---|---|
| 5,324,322 A * | 6/1994 | Grill et al. | 607/118 |
| 5,324,325 A * | 6/1994 | Moaddeb | 607/120 |
| 5,344,438 A | 9/1994 | Testerman et al. | |
| 5,358,514 A * | 10/1994 | Schulman et al. | 607/61 |
| 5,515,848 A | 5/1996 | Corbett, III et al. | |
| 5,531,778 A | 7/1996 | Maschino et al. | |
| 5,571,148 A | 11/1996 | Loeb et al. | |
| 5,649,970 A | 7/1997 | Loeb et al. | |
| 5,824,027 A | 10/1998 | Hoffer et al. | |
| 5,843,127 A | 12/1998 | Li | |
| 5,899,933 A | 5/1999 | Bhadra et al. | |
| 5,902,331 A * | 5/1999 | Bonner et al. | 607/122 |
| 5,922,015 A * | 7/1999 | Schaldach | 607/126 |
| 5,931,864 A | 8/1999 | Chastain et al. | |
| 5,950,970 A * | 9/1999 | Methany et al. | 248/150 |
| 6,051,017 A | 4/2000 | Loeb et al. | |
| 6,093,197 A | 7/2000 | Bakula et al. | |
| 6,129,751 A | 10/2000 | Lucchesi et al. | |
| 6,164,284 A | 12/2000 | Schulman et al. | |
| 6,535,764 B1 * | 3/2003 | Imran et al. | 607/40 |
| 2002/0111659 A1 | 8/2002 | Davis et al. | |
| 2002/0161423 A1 | 10/2002 | Lokhoff et al. | |
| 2002/0193859 A1 | 12/2002 | Schulman et al. | |

FOREIGN PATENT DOCUMENTS

| | | |
|---|---|---|
| WO | WO-98/43700 A1 | 10/1998 |
| WO | WO-98/43701 A1 | 10/1998 |
| WO | WO-00/56394 A1 | 9/2000 |

* cited by examiner

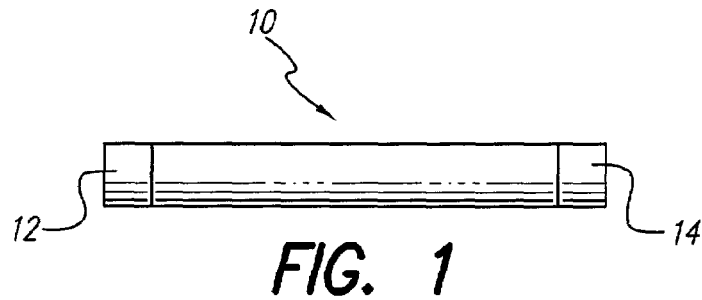
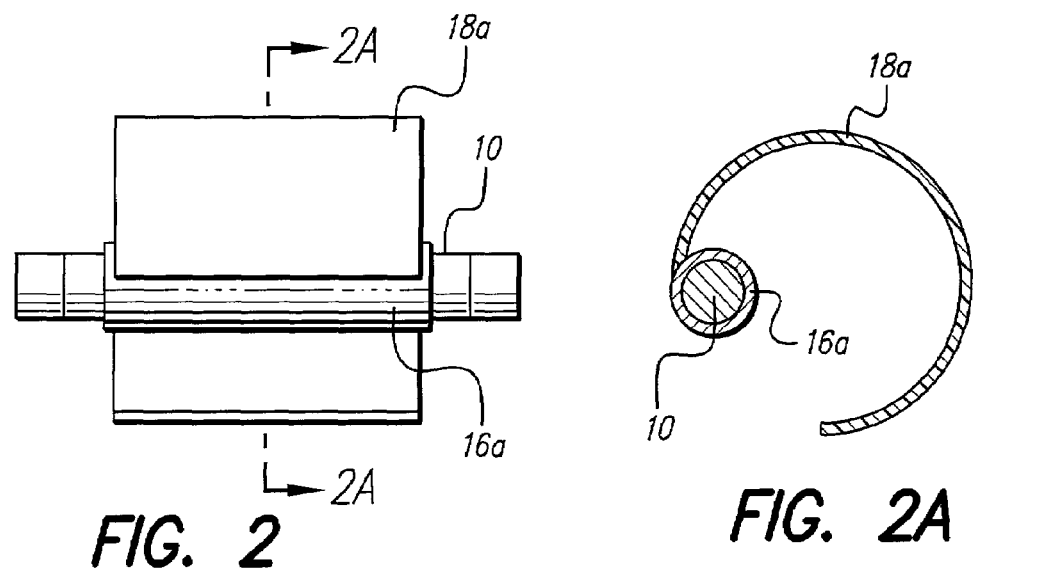
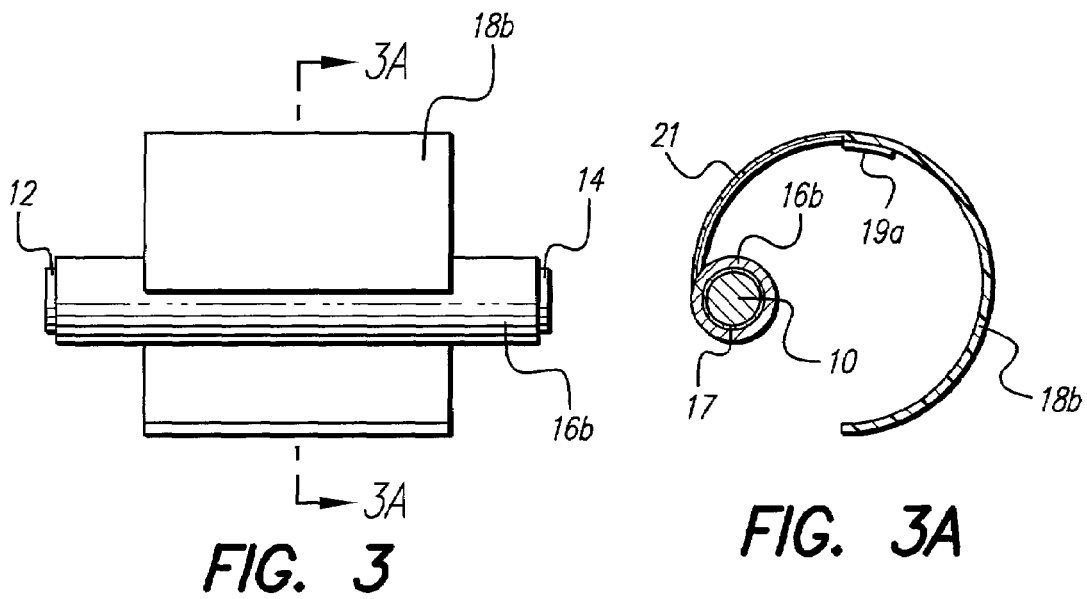

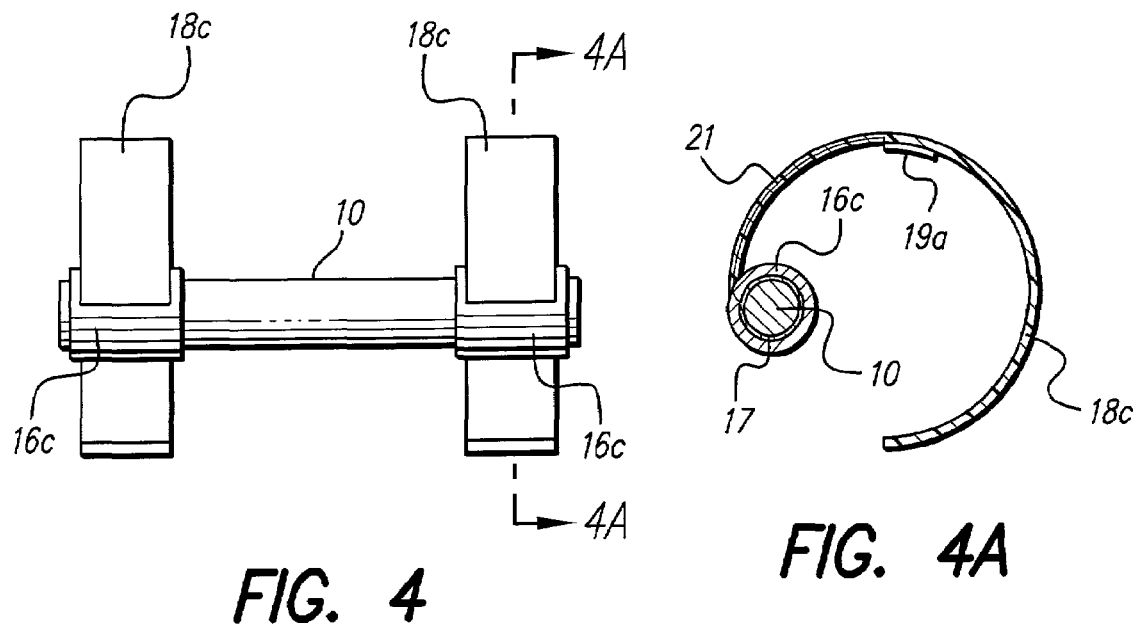
FIG. 4
FIG. 4A
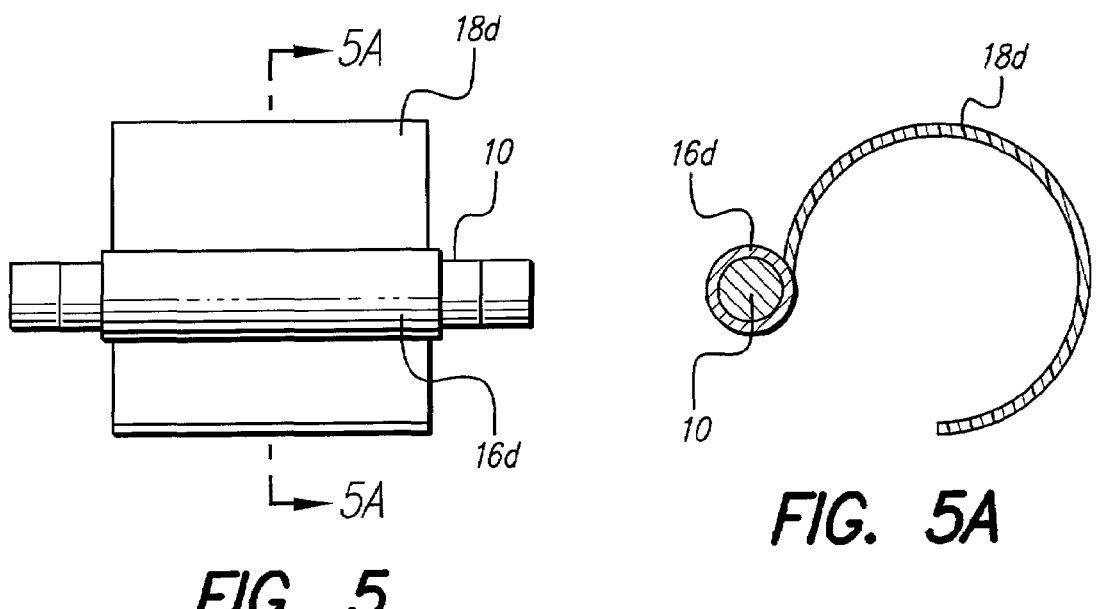
FIG. 5
FIG. 5A

FIXATION DEVICE FOR IMPLANTABLE MICRODEVICES

The present application claims the benefit of U.S. Provisional Application Ser. No. 60/300,401, filed Jun. 22, 2001, which application is incorporated herein by reference.

BACKGROUND OF THE INVENTION

The present invention relates to implantable electrical stimulation devices and more particularly to the fixation of microstimulators included in Peripheral Nerve Stimulation (PNS) systems. Such microstimulators may migrate over time and become ineffective.

Implantable electrical stimulation devices have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Known implantable electrical stimulation systems typically consist of a System Control Unit (SCU), which contains a power source and stimulation electronics, and electrodes connected to the SCU by leads. A number of SCU systems have the advantage of having fixation devices for the electrodes so that the electrodes remain proximal, or even attached, to their target sites of stimulation. For example, some pacemaker electrode leads have tines or fins that act as barbs to hook into the tissue, thereby anchoring the electrodes in place. As another example, the electrode used in the Neuro Cybernetic Prosthesis (NCP®) manufactured by Cyberonics (Houston, Tex.) is a helical electrode that is wound around the vagus nerve in order keep the electrode attached to the stimulation target. Finally, several companies and research institutions, such as Neuro Stream Technologies, Inc. (Anmore, British Columbia, Canada), are investigating cuff electrodes which wrap around the nerve like a cuff, thereby fixing an electrode(s) proximal to a nerve.

While leaded system have been successful in many applications, several potential disadvantages accompany their use. The implantation procedure may be rather difficult and time-consuming, as the electrodes and the SCU must usually be implanted in separate areas, and the lead must be tunneled through body tissue to connect the electrodes to the SCU. Also, the leads are typically thin and rather long and are thus prone to mechanical damage over time. Additionally, many conventional systems typically consist of a relatively large SCU, which can have a negative cosmetic appearance if positioned subcutaneously.

A microminiature electrical stimulator, a microstimulator, is described in U.S. Pat. No. 5,193,539 issued May 16, 1993 for "Implantable Microstimulator." A method for manufacturing the microstimulator is described in U.S. Pat. No. 5,193,540 issued May 16, 1993 for "Structure and Method of Manufacturing of an Implantable Microstimulator." Further teaching is included in U.S. Pat. No. 5,324,316 issued Jun. 28, 1994 for "Implantable Microstimulator." WO 97/29802 published Aug. 21, 1997 for "Improved Implantable Microstimulator and System Employing Same," describes a microstimulator coated with a biocompatible polymeric providing increased strength and therapeutic effects. WO 98/43700 published Oct. 8, 1998 for "System of Implantable Devices for Monitoring And/Or Affecting Body Parameters," describes a system including microdevices, for monitoring and affecting the parameters of a patient's body. WO 98/43701 published Oct. 8, 1998 for "System of Implantable Devices for Monitoring And/Or Affecting Body Parameters," describes a system including a System Control Unit (SCU) and one or more microdevices, for monitoring and affecting the parameters of a patient's body. And, WO 00/56394 published Sep. 28, 2000 for "Ceramic Case Assembly For a Microstimulator" describes a ceramic case for a microstimulator, which case is transparent to an alternating electromagnetic field and offers strength superior to previous case materials. The '539, '540, and '316 patents, and the '802, '700, '701, and '394 PCT publications are incorporated herein by reference.

The microstimulator was developed to solve a number of issues related to implantable stimulation devices, including overcoming some of the disadvantages of a leaded system. The SCU and the electrodes of the microstimulator have been combined into a single microminiature package, thus eliminating the need for a lead. A typical embodiment of a microstimulator is housed in a cylindrical case that is about 3 mm in diameter and between 2 and 3 cm in length. This form factor allows a microstimulator to be implanted with relative ease and rapidity, e.g., by injection or via endoscopic or laparoscopic techniques. Known microstimulators are held in place by the tissue that surrounds the case and do not include means of fixation or stabilization other than certain coatings which may be applied to the surface of the case to allow greater adhesion to the surrounding tissue.

In some PNS applications, the microstimulator is surrounded by soft tissue and is not embedded in, or located very close to, large muscles or other structures that experience significant motion or varying pressure. In such applications, additional means for fixation of the microstimulator is not required. However, in other applications, fixation of the microstimulator may be necessary. For example, some peripheral nerves are located immediately next to, or are embedded within, muscles. Contraction of the muscles may cause the microstimulator to migrate significantly over time. Additionally, the motion of limbs may exert unequal pressures on the microstimulator at almost any location within an extremity, which may also result in migration, especially along the pathway created during implantation.

As yet another example, some nerves are surround by firm but lubricious tissue, and such tissue may not provide sufficient fixation of the microstimulator. The vagus nerve runs through the carotid sheath in the neck, which is surrounded by a number of muscles. The firm, lubricious carotid sheath is likely to offer little adhesion to the microstimulator, and actuation of the surrounding neck muscles may cause significant migration of the microstimulator, especially during the period immediately following implantation.

What is needed is a means for fixation for a microdevice when the cooperation of the case with surrounding tissue is not sufficient to prevent migration.

SUMMARY OF THE INVENTION

The present invention addresses the above and other needs by providing a fixation device for microstimulators. The fixation device may either attach to a microdevice, and cooperate with surrounding tissue to prevent migration of the microdevice, or reside behind the microdevice in the implantation pathway, and thereby prevent retreat of the microdevice through the pathway. In one embodiment, the fixation device comprises a sheath adapted to attach the fixation device to the microdevice, and means for attaching the fixation device to surrounding tissue to prevent migration of the microdevice. Several embodiments of the fixation device exist, each constructed from a non-conducting material, except where specifically noted. Such material may further be resorbable.

In a first embodiment, the fixation device comprises a sheath that fits at least partly around the microdevice, and means for attaching to tissue comprising a somewhat flexible arced grasping member (i.e., arced member), with the sheath residing substantially inside the arc of the grasping member. The grasping member may be distended so that the grasping member may be wrapped around a nerve, muscle, or other body tissue. The sheath grips the microdevice and holds the microdevice proximal to the tissue which is wrapped by the grasping member so that anodes and/or cathodes on the microdevice may reside directly against the tissue.

In a second embodiment, the grasping member of the first embodiment includes at least one electrode which is electrically connected to the microdevice through at least one contact included in the sheath. In the second embodiment, the microdevice electrodes may be exposed or may be completely covered and insulated by the sheath or by a separate coating.

In a third embodiment, the fixation device includes at least two grasping members (as opposed to a single and perhaps relatively larger grasping member as in the first and second embodiments). The grasping members of the third embodiment may be uniform in size or may vary. Some or all of the grasping members may contain electrodes, and the electrodes may be independent or may be linked together in groups.

In a fourth embodiment, the microdevice resides substantially outside of the grasping member. This allows the entire grasping member to maintain uniform contact with the tissue around which the grasping member is wrapped.

In a fifth embodiment, the fixation device includes at least one helix member that wraps around a nerve or other tissue. The helix may contain one or more electrodes, which electrodes are electrically connected to the microdevice through at least one contact included in the sheath. The helices may extend beyond either end of the microdevice, allowing the stimulation currents to be spread farther or to be delivered to more distant targets. Helices may also be wrapped between grasping members to focus the stimulation or sensing on a small target region. The helix and other grasping member may be combined in any number, order, or other combination.

In a sixth embodiment, the fixation device comprises a sheath and at least one extension, wherein the extension includes at least one hole adapted to accept a suture therethrough. The extension may contain one or more electrodes that are electrically connected to the microdevice through at least one contact included in the sheath.

In a seventh embodiment of a fixation device, the fixation is achieved by preventing the retreat of the microdevice through the implantation pathway. The pathway is blocked by an assembly residing in the pathway, behind the microdevice. The assembly may comprise a surgical adhesive or a mechanical blocking device. The assembly may further be a resorbable scaffold.

BRIEF DESCRIPTION OF THE DRAWINGS

The above and other aspects, features and advantages of the present invention will be more apparent from the following more particular description thereof, presented in conjunction with the following drawings wherein:

FIG. 1 shows a microdevice suitable for fixation by the fixation device of the present invention;

FIG. 2 depicts the microdevice residing in a sheath of a first embodiment of the fixation device;

FIG. 2A shows a cross-sectional view of the microdevice residing in the sheath of the first embodiment of the fixation device, taken along line 2A—2A of FIG. 2;

FIG. 3 shows a second embodiment which is similar to the first embodiment, but with the fixation device including at least one electrode;

FIG. 3A shows a cross-sectional view of the microdevice residing in the sheath of the second embodiment of the fixation device, taken along line 3A—3A of FIG. 3;

FIG. 4 shows a third embodiment which is similar to the first embodiment, but with the fixation device including at least two grasping members;

FIG. 4A shows a cross-sectional view of the microdevice residing in the sheath of the third embodiment of the fixation device, taken along line 4A—4A of FIG. 4;

FIG. 5 depicts a fourth embodiment of the fixation device with a microdevice residing therein;

FIG. 5A shows a cross-sectional view of the microdevice residing in the sheath of the third embodiment of the fixation device, taken along line 5A—5A of FIG. 5;

Corresponding reference characters indicate corresponding components throughout the several views of the drawings.

DETAILED DESCRIPTION OF THE INVENTION

Figure 6:
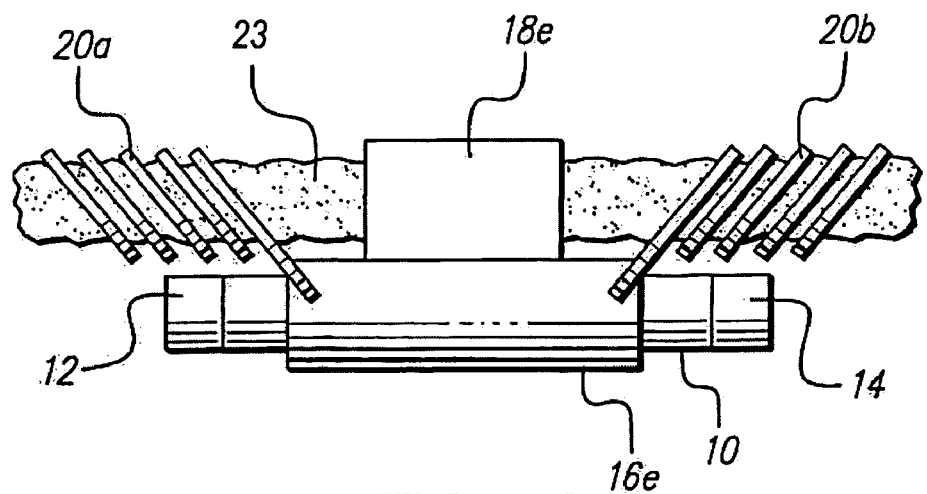
FIG. 6 depicts a fifth embodiment of the fixation device which embodiment includes helices wrapped around a nerve or other body tissue.

The following description is of the best mode presently contemplated for carrying out the invention. This description is not to be taken in a limiting sense, but is made merely for the purpose of describing the general principles of the invention. The scope of the invention should be determined with reference to the claims.

An implantable microdevice 10 shown in FIG. 1 may serve many useful purposes by providing stimulation to or sensing within body tissue. The microdevice 10 includes internal circuitry to receive and process signals, and to provide either sensing or stimulation through an anode 12 at one end, and a cathode 14 at an opposite end. The microdevice 10 is very small to allow minimally invasive implantation. A preferred microdevice 10 is about 2 to 3 cm in length, and about 3 mm in diameter. The characteristics, employment, and manufacturing of an example of the microdevice 10 are described in, e.g., U.S. Pat. No. 5,193,539 issued May 16, 1993 for "Implantable Microstimulator," U.S. Pat. No. 5,193,540 issued May 16, 1993 for "Structure and Method of Manufacturing of an Implantable Microstimulator," U.S. Pat. No. 5,324,316 issued Jun. 28, 1994 for "Implantable Microstimulator," WTO publication WO 97/29802 published Aug. 21, 1997 for "Improved Implantable Microstimulator and system Employing Same," WTO publication WO 98/43700 published Oct. 8, 1998 for "System of Implantable Devices for Monitoring And/Or Affecting Body Parameters," WTO publication WO 98/43701 published Oct. 8, 1998 for "System of Implantable Devices for Monitoring And/Or Affecting Body Parameters," and WTO publication WO 00/56394 published Sep. 28, 2000 for "Ceramic Case Assembly For a Microstimulator." The '539, '540, and '316 patents, and the '802, '700, '701, and 394 publications, were incorporated by reference above.

In some applications, for example Peripheral Nerve Stimulation (PNS), the microdevice 10 may require a fixation device to prevent migration of the microdevice 10 after implantation. In general, the fixation device comprises a holder suitable for holding the microdevice 10, and a means for attaching the fixation device to body tissue. A first embodiment of the fixation device is shown in a side view in FIG. 2, with the fixation device comprising a first sheath 16a which holds the microdevice 10, and a first grasping member 18a to attach the microdevice to a nerve, muscle, or other body tissue.

A cross-sectional view of the first embodiment of a fixation device, taken along line 2A—2A of FIG. 2, is shown in FIG. 2A. A somewhat flexible curved member forms the grasping member 18a, with the sheath 16a residing substantially inside the arc of the grasping member 18a (i.e., most or all of the sheath 16a resides inside the circle defined by that arc of the grasping member 18a). The grasping member 18a is somewhat flexible, i.e., may be distended so that the grasping member 18a may be placed around the tissue. The sheath 16a grips the microdevice 10 and holds the microdevice 10 proximal to the tissue that is wrapped by the grasping member 18a, so that the anode 12 and the cathode 14 reside against the tissue. The sheath 16a may be attached to the microdevice 10 by a tight fit provided by the mechanical cooperation of the sheath 16a and the microdevice 10, or by thermal expansion following assembly. A Titanium Nickel (TiNi) shape memory alloy may be used which grips the microdevice 10 when heated. An adhesive (e.g., surgical adhesive, medical grade cyanoacrylate, medical grade epoxy, etc.) may be used to attach the sheath 16a to the microdevice 10. Other methods of attachment include welding, brazing, injection molding, or shrink wrapping. Those skilled in the art will recognize that the grasping member 18a may generally be much larger than the sheath 16a, slightly larger than the sheath 16a, or smaller than the sheath 16a, depending on the nerve or other tissue that the microdevice 10 is intended to be attached to. The sheath 16a is preferably constructed from silicone, polyimide, or polyurethane. The grasping member 18a is preferably constructed from silicone, polyimide, or polyurethane.

A second embodiment of a fixation device is shown in FIG. 3 in a side view, and in FIG. 3A in a cross-sectional view taken along line 3A—3A of FIG. 3. A second grasping member 18b includes at least one first electrode 19a, which electrode 19a is electrically connected by at least one lead 21 to at least one contact 17 residing on the interior of a second sheath 16b. The contact 17 is adapted to cooperate with the microdevice 10 to provide an electrical connection between the lead 21 and electronics included in the microdevice 10, preferably through contact with the anode 12 or the cathode 14. However, those skilled in the art will recognize that the contact 17 may electrically connect to the microdevice 10 through some other special contact on the exterior of the microdevice 10. In a preferred embodiment, the contact 17 comprises a cylindrical or ring contact.

In the second embodiment, the anode 12 and the cathode 14 may be exposed to tissue, or may be covered and insulated, in whole or in part, by the sheath 16b or by a separate insulator, e.g., a coating. Also, the at least one electrode 19a may be of various shapes. The electrode 19a may cover the entire arc of the grasping member 18b, or only part of the arc. Further, the electrode 19a may extend the length of the grasping member 18b, or only part of the length. The electrode 19a is preferably constructed from platinum, iridium, a platinum/iridium alloy, stainless steel, gold, or titanium nitride (TiN).

A third embodiment of the fixation device is shown in a side view in FIG. 4, and in a cross-sectional view taken along line 4A—4A in FIG. 4A. The third embodiment includes at least two third grasping members 18c (as opposed to a single and perhaps larger grasping member as in the first and second embodiments). The grasping members 18c may be uniform in size or may vary. Some or all of the grasping members may include electrodes 19a, and the electrodes 19a may be independent or may be electrically linked together in groups. The electrode 19a is connected by the lead 21 to the contact 17 as in the second embodiment (FIG. 3A). Those skilled in the art will recognize that various other configurations and combinations of grasping members may be utilized, and a fixation device including these other configurations is intended to come within the scope of the present invention.

A fourth embodiment of the fixation device is shown in a side view in FIG. 5 and in a cross-sectional view in FIG. 5A taken along line 5A—5A of FIG. 5, wherein a fourth sheath 16d resides substantially outside the arc of a fourth grasping member 18d (i.e., most or all of the sheath 16d resides outside the circle defined by that arc of the grasping member 18d). Electrodes may be included in the grasping member 18d as described for FIGS. 3 and 3A above, or the simulation or sensing may be provided solely by the anode 12 and the cathode 14. Further, the sheath 16*d* and grasping member 18*d* may be configured as two or more sheaths and grasping members as described in FIGS. 4 and 4A.

A fifth embodiment of the fixation device is shown in FIG. 6. The fifth embodiment includes at least one helix member, and preferably first and second helix members 20*a* and 20*b*, which wrap around the tissue 23, and may or may not include at least one fifth grasping member 18*e*. The helix members 20*a* and 20*b*, and the grasping member 18*e*, are attached to a fifth sheath 16*e*.

Figure 7:
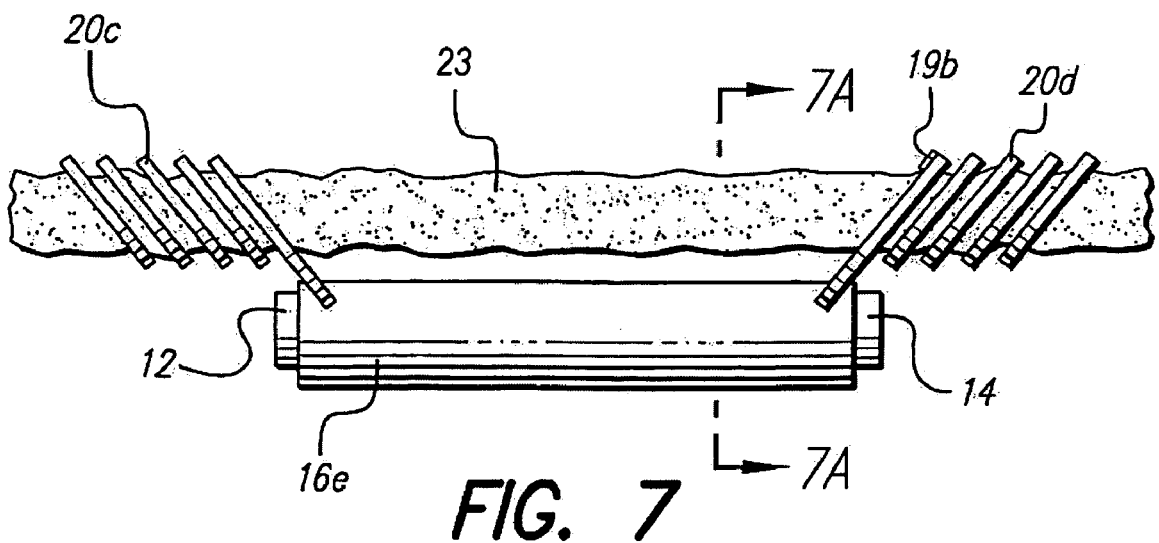
FIG. 7 shows a variation of the fifth embodiment of the fixation device with the helices spread farther apart.
Figure 7A:
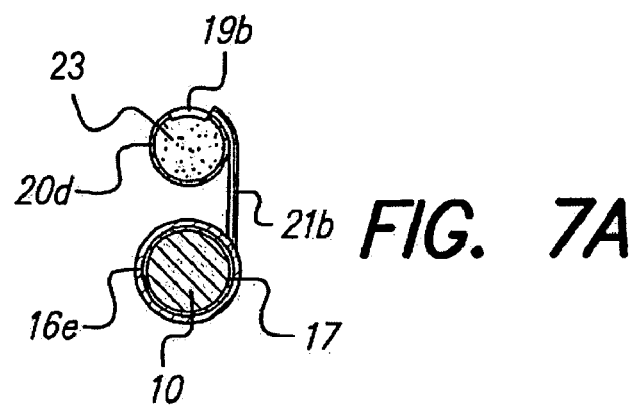
FIG. 7A shows a cross-sectional view of the microdevice residing in the sheath of the fifth embodiment of the fixation device, including an electrode residing in the helix, taken along line 7A—7A of FIG. 7.

Another embodiment of the fixation device including helices is shown in FIG. 7, and in a cross-sectional view in FIG. 7A taken along line 7A—7A of FIG. 7. Helix member 20*c* and 20*d* contain at least one second electrode 19*b*, and the electrode 19*b* is electrically connected by a second lead 21*b* to one of the anode 12 and the cathode 14 through electrical contacts 17 included in the sheath 16. The anode 12 and the cathode 14 may be partially or completely covered by the sheath 16, and any exposed portion of the anode 12 and the cathode 14 may be coated by an additional insulating material. The helix members 20*c*, 20*d* may extend beyond either end of the microdevice 10, allowing the stimulation currents to be spread farther apart, or allowing the stimulation currents to be delivered to more distant targets. Alternatively, the helices may not extend beyond the length of the microdevice 10 (i.e., reside between the ends of the microdevice.)

The helix members 20*c*, 20*d* may also reside between grasping members in embodiments with multiple grasping members (i.e., the fourth embodiment described in FIG. 4 above) to focus stimulation or sensing over a small range of tissue. The helices and other grasping member may be combined in any number, order, or other combination, and one or more grasping members may include one or more electrodes electrically connected to the microdevice 10. Those skilled in the art will further recognize that members other than helices may be attached to a sheath to remotely position electrodes, and these other members are intended to come within the scope of the present invention.

Figure 8:
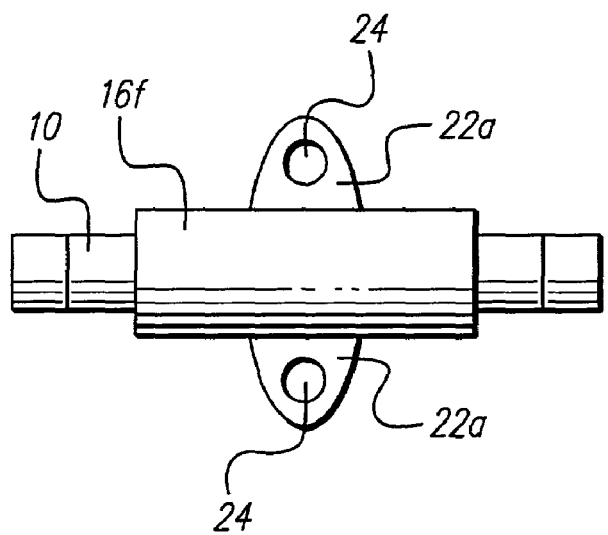
FIG. 8 shows the microdevice residing in a sixth embodiment of the fixation device, which embodiment includes at least one extension adapted to cooperate with sutures.

A sixth embodiment is shown in FIG. 8, wherein the fixation device comprises a sixth sheath 16*f* and at least one extension 22*a*, and wherein the extension 22*a* includes at least one hole 24 adapted to accept a suture therethrough to attach the microdevice 10 to a nerve, muscle, or other tissue. The extension 22*a* may contain at least one electrode that is electrically connected to the anode 12 or the cathode 14 through at least one contact included in the sheath 16*f*, wherein the sheath 16*f* is sufficiently elongated to make electronic contact with at least one of the anode 12 and the cathode 14.

Figure 9:
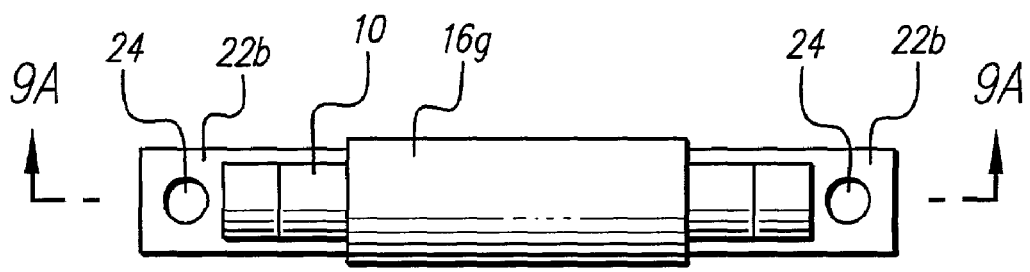
FIG. 9 depicts a variation of the sixth embodiment of the fixation device with a microdevice residing therein.
Figure 9A:
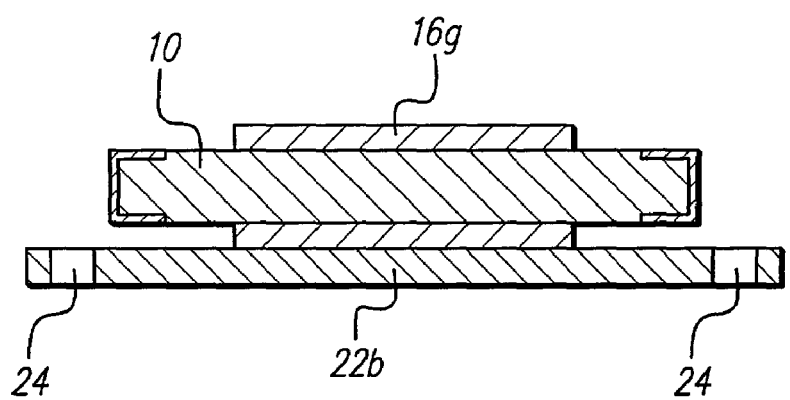
FIG. 9A depicts a cross-sectional view of the fixation device and microdevice taken along line 9A—9A of FIG. 9.

A variation of the sixth embodiment is shown in FIG. 9, and a cross-section taken along line 9A—9A of FIG. 9 is shown in FIG. 9A. A second extension 22*b* runs substantially parallel to the axis of the sheath 16*g*, and extends past both ends of the sheath 16*g*. The holes 24 in the extension 22*b* are adapted to accept a suture therethrough to attach the microdevice 10 to a nerve, muscle, or other tissue.

Extensions defining others shapes will be apparent to those skilled in the art, and these other extensions are intended to come within the scope of the present invention. While holes were described to cooperate with sutures, notches or the like may be provided on opposing sides of the extension to cooperate with sutures. Further, while the microdevice 10 includes the anode 12 at one end, and the cathode 14 at the opposite end, other microdevices with two or more anodes or cathodes in other positions are intended to come within the scope of the present invention, wherein the sheath may be adapted to expose the anode and/or cathode to body tissue, or to insulate the anode or cathode from tissue. Additionally, contacts may be included in the sheath 16*g* which are electrically connected to electrodes in the extension 22*b*, wherein the contacts electrically cooperate with anodes and/or cathodes on a microdevice.

While the fixation device was depicted above as being attached to a microdevice by a sheath comprising a single cylindrical member (i.e., a band), those skilled in the art will recognize that various alternative holders may be used to attach a microdevice to a fixation device. For example, a holder could comprise fingers or loops. These alternative holders are intended to be within the scope of the present invention. Means for attaching the fixation device to tissue have been described above, including a grasping (or arced) member, a helix, and an extension. Those skilled in the art will recognize other means for attaching including staples, pins, ties, and the like. Fixation devices including these, and any other means for attaching to tissue are intended to come within the scope of the present invention.

Figure 10:
FIG. 10 shows a microdevice residing at a distal end of an implantation pathway.

The small size of the microdevice 10 allows the microdevice 10 to be implanted, using for example, a large gauge hypodermic needle, a cannula, or an endoscopic device (e.g., a laparasdcope). This type of implantation leaves an implantation path 26 behind the implanted microdevice 10, as shown in FIG. 10. A seventh embodiment of the fixation device comprises a blocking means adapted to reside behind the microdevice 10 in the path 26.

Figure 11:
FIG. 11 shows a seventh embodiment wherein an assembly comprising an adhesive blocks the retreat of the microdevice along the implantation pathway.
Figure 11A:
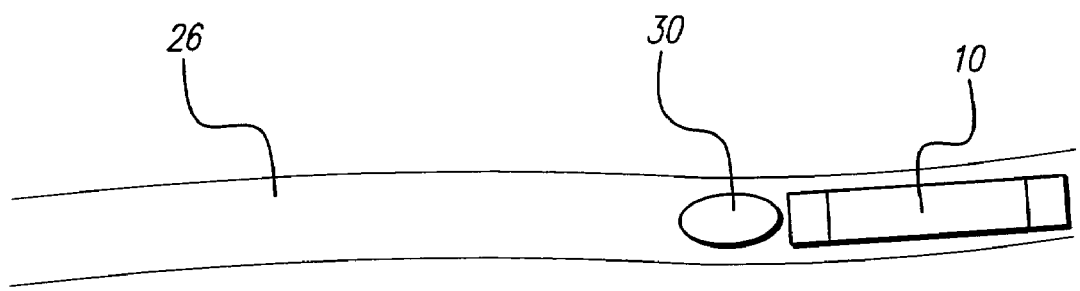
FIG. 11A depicts a breakable vessel containing the adhesive residing next to the microdevice.

A first blocking means comprises a volume of 28 shown in FIG. 11. The adhesive 28 comprises a surgical adhesive suitable for internal use, preferably cyanoacrylate, or acrylics, and more preferably medical grade cyanoacrylate. The adhesive 28 may be deposited into the path 26 using a syringe, cannula, endoscope, or other suitable carrier. In a preferred embodiment, a vessel 30, as shown in FIG. 11A, is adapted to contain the adhesive 28. The vessel 30 is further adapted to be implantable into the path 26 directly behind the microdevice 10. The vessel 30 is thus sized to fit within the path 26, and preferably is about the same diameter as the microdevice 10. Once in position, the vessel 30 is broken, thus releasing the adhesive 28 into the path 26. The vessel 30 is preferable constructed from Synthetic Absorbable Polymer Material (commonly used in sutures), [e.g., polymers such as: Polyglycolic Acid (used in Dexon sutures, prepared from a homopolymer of glycolic acid), Polyglactic Acid (used in Vicryl sutures), Polyglyconate (used in Maxon sutures, prepared from a copolymer of glycolic acid and trimethylene carbonate), or Polydioxanone] or Bioresorbable Hydrogels (e.g., Hyaluronan) and may be constructed from other resorbable material.

Figure 12:
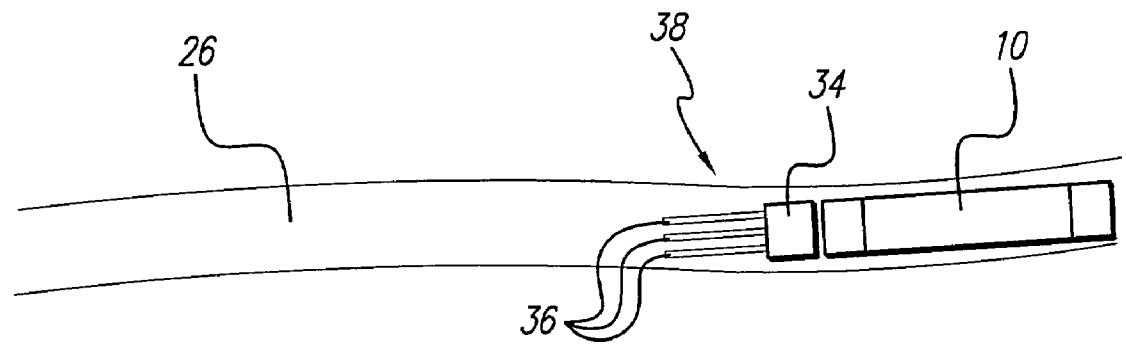
FIG. 12 shows an assembly comprising a blocking device with a retracted fan residing in the implantable pathway adjacent to the microdevice.

A second blocking means is a mechanical assembly 38 shown in FIG. 12. The assembly 38 includes a body 34 and fan or prongs 36. The fan 36 is shown folded to allow insertion into the path 26 (the fan 36 expands when not restrained.) In the folded state, the fan 36 may easily be inserted along the path 26. The fan 36 preferably comprises 2 to 16 tines or prongs that are preferably 1 to 20 mm in length. The body 34 is preferably constructed from metal (e.g., Platinum, Titanium, etc.), silicone, ceramic, or resorbable material. The fan 36 is preferably constructed from metal (e.g., Platinum, Titanium, etc.), silicone, ceramic, or resorbable material (similar to Greenspring and other vascular embolism filters.)

Figure 12A:
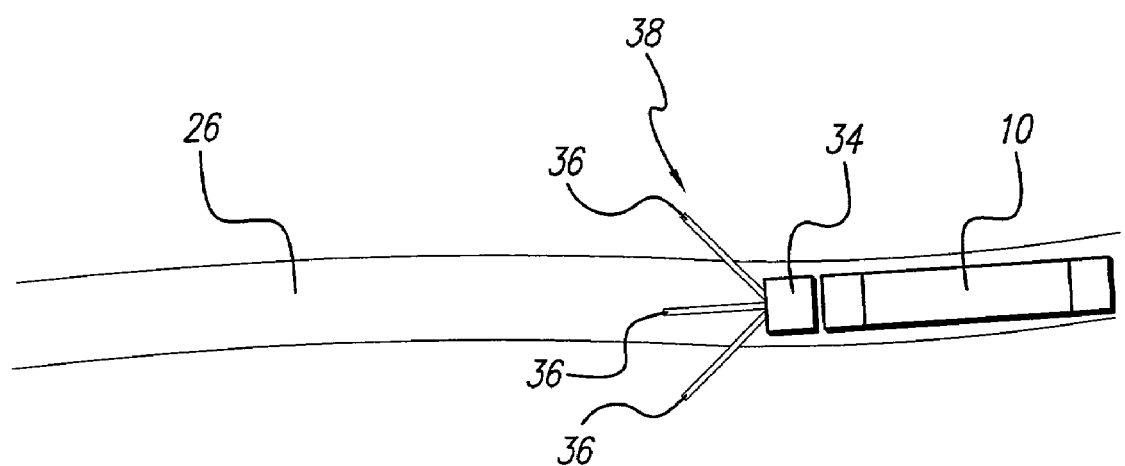
FIG. 12A depicts the blocking device with the fan extended.

A view of the expanded (i.e., no longer restrained) fan 36 is depicted in FIG. 12A. Thus deployed, the fan 36 will resist retreat along the path 26, and thus retain the microdevice 10 in place. Further, the assembly 38 may be adapted to be attachable to the microdevice 10.

Those skilled in the art will recognize that a variety of other structures may be utilized to attach the body 34 to tissue (e.g., barbs, anchor, etc.), and these alternative embodiments, and others, of a means for attaching the body 34 to the target tissue are intended to come within the scope of the present invention.

All exposed surfaces of all embodiments of the fixation device are intended to be manufactured from biocompatible materials, and more preferably, all materials in the fixation device are biocompatible. Any portion of the fixation device may be resorbable, or the entire fixation device may be resorbable, wherein the length of time over which resorption occurs may be almost immediate or may extend over weeks, months, or even years. The fixation device or portions thereof may further elute medications or other substances, e.g., corticosteroids to reduce inflammation or glial cell line-derived neurotrophic factor (GDNF) to promote nerve healing and growth.

In one method of implanting the microdevice and fixation device, the microdevice is placed in the sheath of the fixation device prior to any surgical procedure. The target nerve or other target tissue is exposed and identified, preferably through a minimally invasive procedure but alternatively through a more invasive surgical procedure, and the target tissue may be dissected from surrounding tissues if necessary or desired. The grasping member(s) and/or helix(ces) are distended and wrapped around the tissue such that they enclose much or all of the tissue when released. Alternatively, sutures are placed through one or more of the suture holes in order to hold the fixation device in place. The proper positioning is verified preferably by stimulating through one or more of the electrodes in contact with the tissue (in cases where the microdevice is a microstimulator) or alternatively by recording from one or more of the electrodes in contact with the tissue (in cases where the microdevice is a microsensor).

In an alternative embodiment of the method, the fixation device may be implanted and attached in place prior to the insertion of the microdevice into the sheath. If the fixation device includes electrode(s), once the fixation device is in place, recording and/or stimulation may be performed via an electrode(s), prior to the insertion of the microdevice into the sheath, to verify that the electrodes are in electrical contact with the target tissue (i.e., proper fixation). Following attachment of the fixation device, and verification of proper fixation if applicable, the microdevice is inserted into the sheath. Following insertion of the microdevice, further recording and/or stimulation may be performed via an electrode(s) on the fixation device and/or the microdevice.

The use of the adhesive 28 to retain the microdevice 10 may be most appropriate when the microdevice 10 is implanted in a minimally invasive manner using, for example, a syringe, a cannula, or an endoscope. In such case, the adhesive 28 may also be deposited behind the microdevice 10 using the same syringe, cannula, or endoscope. When the adhesive 28 is provided in a vessel 30, the vessel 30 may also be implanted behind the microdevice 10 using the syringe, cannula, or endoscope.

The implantation of the assembly 38 is preferably performed through the same syringe, cannula, or endoscope used to implant the microdevice 10. The assembly 38 is inserted into the syringe, cannula, or endoscope with the fan 36 folded straight so that the total diameter of the assembly 38 is no greater than the microdevice 10. When the assembly 38 is in place, and the syringe, cannula, or endoscope is removed, the fan 36 is free to spring outward and cooperate with the walls of the implantation path 26 to block the retreat of the microdevice 10.

It is thus seen that in each embodiment of the fixation device described herein, there is provided either (1) a holder (e.g., a sheath) for attaching the fixation device to a microdevice, and a means for attaching the fixation device to a nerve or other body tissue, thus preventing migration of implantable microdevices; or (2) a blocking means to retain the microdevice in it's intended position in the implantation path. Some embodiments further include contacts to make an electrical connection with one or more electrodes on the surface of the microdevice, and additional electrodes to provide stimulation or sensing of tissue separated from the microdevice.

While the invention herein disclosed has been described by means of specific embodiments and applications thereof, numerous modifications and variations could be made thereto by those skilled in the art without departing from the scope of the invention set forth in the claims.

What is claimed is:

1. An implantable device including a fixation device with an implantable microdevice for stimulating tissue, said microdevice comprising a case, comprising:
    a flexible, arced grasping member comprising a sheet of material having a first edge and a second edge, said sheet being curved into an unclosed cylindrical shape with said first and second edges being separated by an open space running a full length of said cylindrical shape;
    a holder configured to hold said microdevice, said holder being disposed along a length of said first edge of said sheet; and
    said implantable microdevice in said holder configured to deliver a stimulus to said tissue, said microdevice being secured in position relative to said tissue by said grasping member and said holder.

2. The device of claim 1 wherein the flexible, arced grasping member comprises at least two fingers.

3. The device of claim 1 wherein the holder comprises at least two loops.

4. The device of claim 1 wherein the holder comprises a sheath.

5. The device of claim 1 wherein the flexible arced member is configured to reach substantially around the body tissue.

6. The device of claim 5 wherein the holder resides substantially within the arc of the arced member.

7. The device of claim 5 wherein the holder resides substantially outside the arc of the arced member.

8. The device of claim 5 wherein the arced member comprises at least two arced members spaced along a length of the microdevice.

9. The device of claim 8 wherein the arced members are uniform in size.

10. The device of claim 8 wherein the arced members vary in size.

11. The system of claim 1 wherein the flexible arced member comprises at least one electrode configured to provide stimulation to the body tissue, and wherein the holder includes at least one contact configured to electrically cooperate with the microdevice to electrically connect the microdevice to the electrode.

12. The device of claim 1 wherein the fixation device is configured to elute at least one medication.

13. The device of claim 1 wherein at least one of the set consisting of the holder and the arced member is made from a resorbable material.

14. The device of claim 1 wherein the microdevice is a microstimulator element of a Peripheral Nerve Stimulation (PNS) system.

15. The device of claim 1 wherein the arced member comprises silicone, polyimide, or polyurethane.

16. The device of claim 1 further comprising at least one helical member connected to the holder for engaging the body tissue along with the flexible arced member.

17. The device of claim 1, wherein said sheet is substantially rectangular in shape.

18. A method of using an implantable microdevice with a fixation device comprising a holder for the microdevice disposed on a flexible arced member having an opening along a length thereof for engaging body tissue, comprising;
placing the body tissue in a space within and defined by the arced member by passing the body tissue through the opening running along the length of the arced member such that the arced member is placed around the body tissue; and
placing the microdevice in the holder,
wherein the arced member is placed on the body tissue before the microdevice is placed in the holder.

19. A system for an implantable microdevice, comprising:
means for grasping an elongated body tissue, the means having an opening along a length thereof so that the means for grasping can be slipped around the elongated body tissue by passing the tissue through the opening such that the means for grasping curls around the tissue; and
means for holding the microdevice disposed on the means for grasping.

20. The system of claim 19 wherein the means for grasping comprises at least two arced members spaced along a length of the microdevice.

21. The system of claim 19 wherein the means for grasping further comprising at least one electrode for providing stimulation to the body tissue by connecting with the microdevice.

22. The system of claim 19 wherein the system is configured to elute at least one medication.

* * * * *